US00PP09500P

United States Patent [19]

Ebihara

[11] Patent Number: Plant 9,500

[45] Date of Patent: Apr. 9, 1996

[54] HYDRANGEA PLANT NAMED 'FRAU REIKO'

[75] Inventor: Hiroshi Ebihara, Ninomiya, Japan

[73] Assignee: Miyoshi & Co. Ltd., Tokyo, Japan

[21] Appl. No.: 412,975

[22] Filed: Mar. 29, 1995

[51] Int. Cl.[6] ..... A01H 5/00

[52] U.S. Cl. ..... Plt./67.1

[58] Field of Search ..... Plt./67.1

*Primary Examiner*—James R. Feyrer
*Attorney, Agent, or Firm*—James R. Cypher

[57] ABSTRACT

This invention relates to a new and distinct cultivar of *Hydrangea macrophylla* subsp. *macrophylla* var. *normalis* (Thunb.) named 'Frau Reiko' which originated as a seedling from the inventor's controlled hybridization of the cultivars *Hydrangea macrophylla* and *Hydrangea macrophylla* DC var. *hortensia* 'Silver–Edge'. 'Frau Reiko' is a lace cap Hydrangea characterized by an inflorescence consisting predominently of non-sepalous florets in the center with some open florets on the perimeter. The non-sepalous buds open to provide a pink or violet background to the exposed white pollen. The color of the sepalous buds, is predominately blue or pink with narrow delineated, finely serrated white edges. The pigmentation begins at the apex and fades slightly as it progresses across the length and width of the sepals, and then turns white 5 mm or less from edge. Dark pigmentation ocassionally reaches the edge of the sepal the apex. The sepals are also characterized by their finely serrate edges. The new variety of Hydrangea as described herein is characterized by its form of inflorescence, pattern of pigmentation in the sepals, compact growth habit, the ease with which it can be forced in a greenhouse, and its long lasting flowers.

2 Drawing Sheets

BACKGROUND OF THE INVENTION

This invention relates to a new and distinct cultivar of florist-type hydrangea plant of the Saxifragaceae family. The botanical name of the plant is *Hydrangea macrophylla* subsp. *macrophylla* var. *normalis* (Thunb.) names 'Frau Reiko'. The new cultivar originated as a seedling from the breeding efforts of the inventor. A distinct sepal pigmentation pattern was developed through the hybridization of the cultivars 'Silver Edge' and *Hydrangea macrophylla*. 'Frau Reiko' was discovered and selected as one flowering plant within the progeny of the stated parentage in a controlled environment in Tochigi-Prefecture, Japan. This new cultivar has been successfully asexually reproduced under controlled environmental conditions at a nursery in Half Moon Bay, Calif. under the direction of the inventor over a three year period with its distinguishing characteristics remaining stable.

The new variety of Hydrangea as herein described is termed a lace cap Hydrangea. In a lace cap Hydrangea the non-sepalous florets dominate the inflorescence with the sepalous florets occurring only at the perimeter, producing a flat-topped inflorescence, which is commonly described as open and lacy. Sepal pigmentation of individual *Hydrangea macrophylla* plants depends on the nutrients and pH of the growing medium. In the new variety described herein the non-sepalous buds open to provide a pink or violet background to the exposed white pollen. In the sepalous buds, the sepal color is predominately blue or pink with a narrow, delineated, finely serrated white edge. The pigmentation is darkest at the apex and fades slightly as it progresses across the length and width of the sepals, and then turns white as far as 8 mm from edge, but mostly 5 mm or less is observed. Color pigmentation sometimes reaches the edge of the sepal at the apex. The sepals are also characterized by their finely serrated edges. The new variety of Hydrangea as described herein is further characterized by its compact growth habit, the ease with which it can be forced in a greenhouse, and its long lasting flowers. Mature flowers slowly fade to cream, then green and ultimately brown with age.

Asexual reproduction was first accomplished when vegetative cuttings were taken by the inventor from the initially selected plant. Examination of asexually reproduced, successive generations grown in a controlled environment at Half Moon Bay, Calif. show that the combination of characteristics as herein disclosed for 'Frau Reiko' is firmly fixed. Asexual reproduction of successive generations at Half Moon Bay was achieved by taking vegetative cuttings from selected plants over three years. Each new generation over the three years retained the combination of characteristics as herein disclosed for 'Frau Reiko'.

DESCRIPTION OF THE DRAWINGS

The accompanying drawings consist of color photographs that illustrate the typical plant form, including the inflorescence, foliage, and unique sepal pigmentation pattern. These color photographic drawings show the pink form of the new cultivar. The colors are represented as truly as possible using conventional photographic procedures. 'Frau Reiko' is shown with a pink and white sepal pigmentation pattern, but a blue and white pigmentation pattern is also possible by manipulation of the nutrient amendments and the pH of the growing medium.

DESCRIPTION OF THE NEW PLANT

Figure 1:
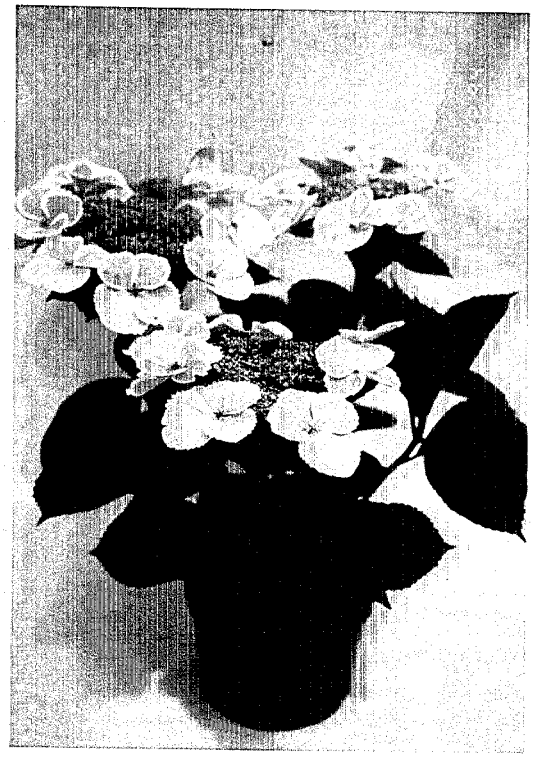
FIG. 1 is a view of the entire plant showing its form, compact growth habit, dark green foliage, inflorescence consisting of mostly non-sepalous lacy flower buds with open sepals on the perimeter, and color pattern of the plant.
Figure 2:
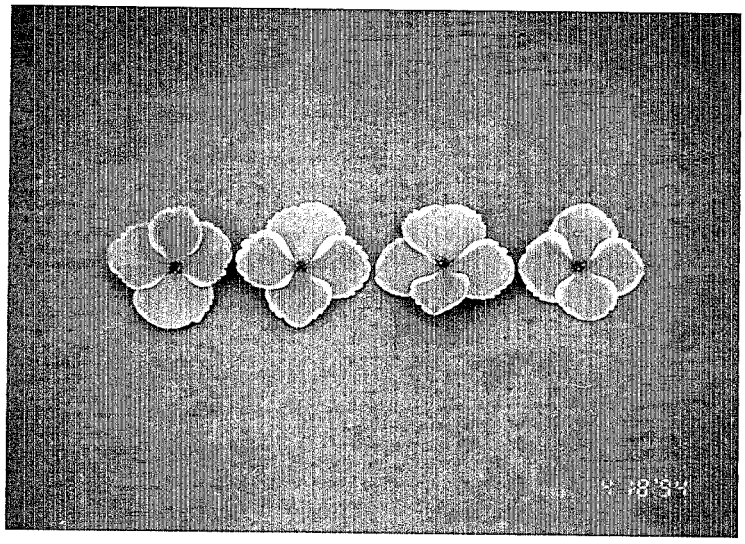
FIG. 2 is a close-up view of the individual florets illustrating the delineated, white, finely serrated edges and predominate coloration pattern (color pigmentation is darkest at the apex and fades slightly as it progresses across the length and width of the sepals).
Figure 3:
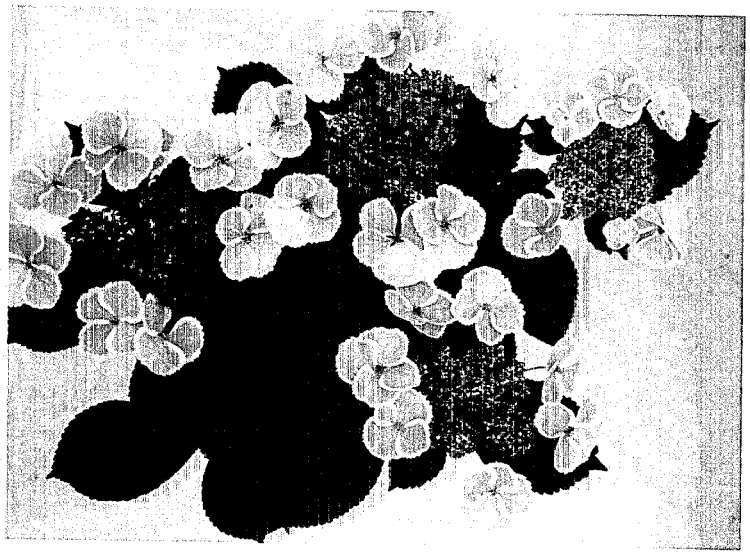
FIG. 3 is a view of the plant taken from above showing how the non-sepalous flower buds dominate the inflorescence at full bloom.
Figure 4:
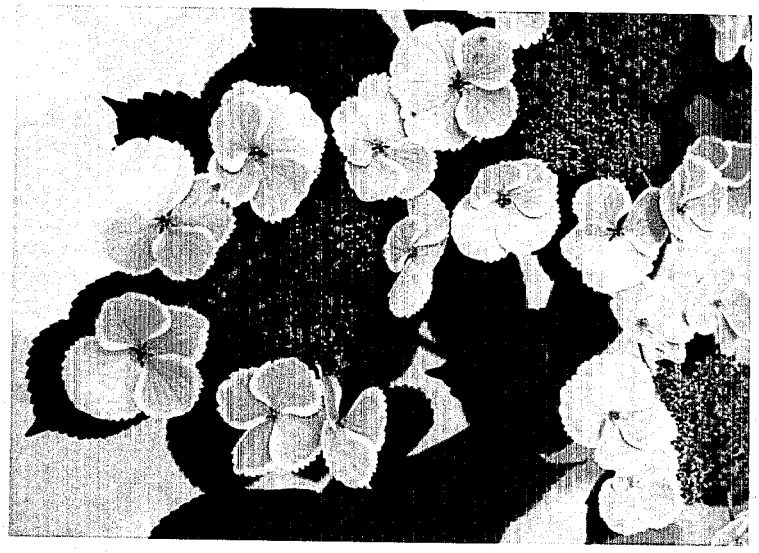
FIG. 4 is a close-up view of the inflorescence illustrating how the non-sepalouse flower buds open and provide a pink to violet background to the exposed white pollen.

'Frau Reiko' has not been observed under all possible environmental conditions. The phenotype may vary significantly with variations in environment such as temperature, light intensity and day length. The following is a detailed description of the new cultivar as forced under the prevailing daylengths at Half Moon Bay, Calif., during the winter months, under commercial greenhouse conditions, as would be appropriate for the sale of the cultivar in the spring. The color determinations were made with The Royal Horticultural Society (R.H.S.) Colour Chart.

THE PLANT

Origin: Seedling.

Parentage:

*Seed parent.*—*Hydrangea macrophylla.*

*Pollen parent.*—*Hydrangea macrophylla* DC var. *hortensia* 'Silver-Edge'.

Classification:

*Botanic.*—*Hydrangea macrophylla* subsp. *macrophylla* var. *normalis* (Thunb.) 'Frau Reiko'.

*Commercial.*—Florist Hydrangea 'Frau Reiko'.

Form: Upright, compact shrub.

Height: Flowering shoots grow as high as 30 cm, non-flowering shoots grow as high as 40 cm.

Growth: Upright, vigorous growth habit; forced without growth regulation.

Stems: Lenticels edged in red; lateral buds are reddish; reddish coloration above but rarely below leaf attachment sites.

Branching: Excellent.

Foliage: Abundant.

*Size of leaf.*—As large as 133 mm long by 86 mm wide.

*Shape of leaf.*—Elliptic with acute base and apex; margins are serrated.

*Texture.*—Glabrous; veins dominate on the underside of the leaf and are sunken on the leaf surface.

*Color.*—Upper side is R.H.S. 137 A (green group); upper side covered by flower is R.H.S. 147 A (yellow-green group); under side is R.H.S. 137 C (green group); veins are R.H.S. 145 D (yellow-green group).

*Petioles.*—As long as 2.5 cm.

THE BUD

Form: Globose; with 4 to 5 connate petals. The inflorescence consists chiefly of non-sepalous buds. As many as but not more than 8 marginal buds are imbricated by sepals.

Size: 3 mm.

Aspect: Smooth.

Rate of opening: Buds with sepals opening more slowly than buds without sepals.

Sepals: Imbricated; finely serrated. Early pigmentation ranges from R.H.S. 145 B to 150 D (yellow-green group). Buds without sepals when mature are pink to violet pink giving a colorful background for the white pollen.

Arrangement: Borne on 3, 4 or 5 branched panicles, usually 5.

INFLORESCENCE

Time of blooming: Forced in 70 to 80 days at 15.5° C. night temperature.

Form: Paniculate. 100 or more individual flowers (florets) per inflorescence. Both sterile, sepalous florets and fertile, non-sepalous florets borne on the same panicle.

Size of Inflorescence: Individual inflorescence size is dependent on the number of inflorescences. Large inflorescences have been measured with a 22 cm. diameter on a multiflowered plant.

Shape: Essentially a flat cluster of numerous small florets. Sepals elongate and color as the inflorescence matures.

Appearance: Showy.

Persistence: 4 plus weeks.

Fragrance: Faintly sweet when in full bloom.

Fruit: None.

Reproductive organs:

*Stamens.*—7 to 9 stamens. Pollen is white.

*Stigma.*—1 three-pronged stigma.

Sepalous florets:

*Number of sepals.*—4 or 5 sepals per floret, usually 4.

*Aspect of sepals.*—Smooth.

*Shape of sepals.*—Reniform with acuminate apex. Edges finely serrated.

*Size of sepals.*—Usually 1 dominant sepal, 2 smaller but equally-sized sepals, and 1 small sepal. Large sepals can measure as much as 54 mm wide by 42 mm long.

*Coloration of sepals.*—Predominately pink or blue with narrow, delineated white edges. The pigmentation fades slightly as it progresses across the length and width of the sepals, and then turns white as far as 8 mm from edge, but mostly 5 mm or less is observed. Color pigmentation sometimes reaches the edge of the sepal, at the apex. As inflorescences age the coloration of entire sepal fades to cream, then green, and then brown. Sepal color is not detailed using the R.H.S. Colour Chart as the sepal color is determined by the soil pH and nutritional amendments supplied.

I claim:

1. A new and distinct hybrid plant variety of the Saxifragaceae family substantially as herein shown and described.

* * * * *